United States Patent
Katsuyama et al.

[11] Patent Number: 5,753,691
[45] Date of Patent: May 19, 1998

[54] AGENTS FOR INHIBITING THE PRODUCTION OF IL-1β AND THE RELEASE OF TNFα

[75] Inventors: Koichi Katsuyama; Masato Ariga. both of Ohimachi; Yukio Saito. Tokyo; Shigeo Hatanaka. Ohimachi; Kenichi Momose. Tokyo. all of Japan

[73] Assignee: Nisshin Flour Milling Co., Ltd., Tokyo, Japan

[21] Appl. No.: 577,338

[22] Filed: Dec. 22, 1995

[30] Foreign Application Priority Data

Dec. 26, 1994 [JP] Japan ............... 6-322073

[51] Int. Cl.$^6$ .............. A61K 31/445; A61K 31/40
[52] U.S. Cl. .............. 514/423; 514/326; 514/408; 514/421; 514/422; 514/424
[58] Field of Search ............... 514/424, 408, 514/326, 421, 423, 422

[56] References Cited

FOREIGN PATENT DOCUMENTS

| | | |
|---|---|---|
| 0 412 058 A1 | 2/1991 | European Pat. Off. . |
| 61-229801 | 10/1986 | Japan . |
| 61-230798 | 10/1986 | Japan . |
| 2-225458 | 9/1990 | Japan . |

OTHER PUBLICATIONS

Database WPI, Derwent Publications Ltd., AN 90–070409, XP002001828 & JP-A-02 022 263. (Meiji Seika Kaisha), 25 Jan. 1990, Abstract.

CA: vol. 115. No. 7 71387k Giannessi et al., Aug. 1991.

*Primary Examiner*—Theodore J. Criares
*Attorney, Agent, or Firm*—Oblon, Spivak, McClelland, Maier & Neustadt, P.C.

[57] ABSTRACT

The pharmaceutical use of 1-cinnamoyl-2-pyrrolidinone derivatives having the activities to inhibit the production of IL-1β and the release of TNFα. Those derivatives are useful in the treatment or prophylaxis of the diseases such as chronic rheumatism and sepsis.

4 Claims, No Drawings

AGENTS FOR INHIBITING THE PRODUCTION OF IL-1β AND THE RELEASE OF TNFα

FIELD OF THE INVENTION

This invention is concerned with new pharmaceutical use of 1-cinnamoyl-2-pyrrolidinone derivatives having the activities to inhibit the production of Interleukin-1β (IL-1β) and the release of Tumor Necrosis Factor α (TNFα).

BACKGROUND OF THE INVENTION

IL-1β is a protein produced mainly from immunocompetent cells such as macrophages and neutrophils, which is an important factor for immune response. Also, it is known to be a factor playing a central role in the inflammatory process or a factor participating in many vital reactions such as hematopoiesis, internal secretion and nervous system.

For instance, there has been recently clarified the relationship between IL-1β and inflammatory diseases such as chronic rheumatism. IL-1β was detected in the synovial membrane of patients suffering from chronic rheumatism. It was reported that the IL-1β level in synovial fluid correlated with observations on the local inflammation.

The 1-cinnamoyl-2-pyrrolidinone derivatives of the formula

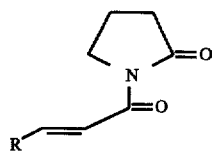

wherein R represents a phenyl group; a phenyl group substituted by a $C_1-C_4$ alkoxy group or a nitro group; or a pyridyl group, are known as a plant growth regulator by Japanese Patent Kokai Sho 61-229801 (JPA 61229801), as a methane fermentation promoter by Japanese Patent Kokai Sho 61-230798 (JPA 61230798) and as a nootropic agent by Japanese Patent Kokai Hei 2-225458 (JPA 2225458). However, there is no reference about other pharmaceutical uses of such derivatives.

Steroidal agents and non-steroidal anti-inflammatory agents have been used for the treatment of inflammatory diseases such as chronic rheumatism. Steroidal agents can achieve remarkable improvement in various symptoms of inflammatory diseases, but they present the problems that drug tolerance may be developed by administration over a prolonged period of time and that side-effects, sometimes serious, such as gastrointestinal disturbance, dermatopathy and nephritis may be caused. Non-steroidal agents can temporarily inhibit inflammatory symptoms, but they cannot radically cure inflammatory diseases.

DISCLOSURE OF THE INVENTION

In view of such circumstances, we have investigated further medical use of known 1-cinnamoyl-2-pyrrolidinone derivatives and found that they possess potent activities to inhibit the production of IL-1β and the release or liberation of TNFα, which are useful as a therapeutic agent for chronic rheumatism and sepsis.

Thus the present invention provides a method of inhibiting the production of IL-1β in a mammal which comprises administering to the mammal an effective amount to inhibit said production, of a compound of the formula or the pharmacologically acceptable salts thereof

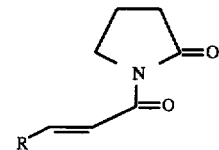

wherein R represents a phenyl group; a phenyl group substituted by a $C_1-C_4$ alkoxy group or a nitro group; or a pyridyl group.

The invention also provides a method of inhibiting the release of TNFα in a mammal which comprises administering to the mammal an effective amount to inhibit said release, of the compound of the above formula or the pharmacologically acceptable salts thereof.

In another aspect, the present invention provides an agent for inhibiting the production of IL-1β and an agent for inhibiting the release of TNFα which comprises said compound or the pharmacologically acceptable salt thereof as an active agent. In particular, those agents are useful as the therapeutic agent for chronic rheumatism and sepsis.

In the above formula, the $C_1-C_4$ alkoxy group includes those derived from straight or branched alkyl of 1-4 carbon atoms, e.g. methoxy, ethoxy, n-propoxy, isopropoxy, n-butoxy, isobutoxy and tert.-butoxy.

Representative examples of the present pyrrolidinone derivatives are shown by the following structures.

| Compound No. | R |
|---|---|
| 1 | phenyl |
| 2 | o-methoxyphenyl |
| 3 | m-methoxyphenyl |
| 4 | p-methoxyphenyl |
| 5 | 3,4-dimethoxyphenyl |
| 6 | 3,4,5-trimethoxyphenyl |
| 7 | o-nitrophenyl |
| 8 | m-nitrophenyl |
| 9 | p-nitrophenyl |
| 10 | 2,4-dinitrophenyl |
| 11 | 2,4,6-trinitrophenyl |
| 12 | 2-pyridyl |
| 13 | 3-pyridyl |
| 14 | 4-pyridyl |

If desired, the pyrrolidinone derivatives of the above formula (R=pyridyl) may be converted, with pharmacologically acceptable acids, to the corresponding acid addition salts which are included within the scope of this invention. Examples of the acid addition salts include those with a mineral acid such as hydrochloric acid, sulfuric acid, hydrobromic acid and phosphoric acid; those with an organic sulfonic acid such as methane sulfonic acid, benzenesulfonic acid and p-toluenesulfonic acid; and those with an organic carboxylic acid such as acetic acid, propionic acid, oxalic acid, succinic acid, maleic acid, fumaric acid, lactic acid, tartaric acid, malic acid and citric acid.

The pyrrolidinone derivatives of the above formula having the activities to inhibit the production of IL-1β and the release of TNFα can be prepared by a variety of processes depending upon their species. The salts of said derivatives can be prepared by a conventional salt-forming process.

The pyrrolidinone derivatives of the present invention possess a potent activity to inhibit the production of IL-1β, with low toxicity, which are useful for the prophylaxis or therapy of various diseases in which IL-1β would participate, such as chronic rheumatism, rheumatic polyarthritis, sepsis, systemic lupus erythematous, systemic scleroderma, Behcet's disease, periarteritis nodosa, colitis ulcerosa, active chronic hepatitis, glomerular nephritis, ostearthritis, gout, atherosclerosis, psoriasis, atopic dermatitis and osteoporosis.

Further, the pyrrolidinone derivatives possess the activity to inhibit the release of TNFα, which are useful for the prophylaxis or treatment of the diseases wherein TNFα would participate in the pathological progress. Such diseases include acquired immune deficiency syndrome (AIDS), in addition to the diseases in which IL-1β would participate, e.g. chronic rheumatism, rheumatic polyarthritis, sepsis and atopic dermatitis.

A dose of the pyrrolidinone derivative to exert an effective activity is usually 5 mg to 6 g per adult daily, preferably 10–300 mg. Administration of said derivative includes oral, intravenous, subcutaneous, intramuscular, intrarectal or intra-articular administrations; oral, intra-articular and intravenous administrations being preferable.

The pyrrolidinone derivatives can be formulated for administration by any conventional methods for forming pharmaceutical preparations.

Examples of pharmaceutical preparations include solid preparations such as tablets, granules, powders, hard capsules and soft capsules, and liquid preparations.

The solid preparations may contain any conventional components such as binders, e.g. dextrin, hydroxypropylcellulose, hydroxypropylmethylcellulose, polyvinyl pyrrolidone and macrogol; excipients, e.g. lactose, corn starch, calcium phosphate and magnesium aluminum metasilicate; lubricants, e.g. calcium stearate and talc; disintegrators, e.g. carboxymethyl cellulose and crystalline cellulose. The tablets may be coated by any methods known in the art.

The liquid preparations include aqueous or oily suspensions, emulsions, solutions, syrups, elixirs and others. Alternatively, they may be any dried products capable of being redissolved in water or other suitable vehicle before use. Such liquid preparations may contain any conventional additives such as suspending agents, e.g. sorbitol syrup, carboxymethyl cellulose, gelatin, hydroxyethyl cellulose, aluminium stearate gel and hydrogenated edible oils; emulsifying agents, e.g. lecithin, glycerol monostearate and acasia; non-aqueous vehicles, e.g. palm oil, propylene glycol and ethanol; and antiseptics, e.g. ethyl p-hydroxybenzoate and sorbic acid.

Dosage forms for parenteral administration include injections and suppositories.

Injections may be prepared by a conventional method, if required, by incorporating in the active compounds a pH adjusting agent, a buffer, a stabilizer, a preservative, a solubilizing agent and the like.

This invention is further illustrated by the following examples.

EXAMPLE 1

The pyrrolidinone derivatives of the present invention were evaluated for the activity to inhibit the production of IL-1β, in accordance with the following method.

The THP-1 cells derived from human peripheral blood (ATCC TIB202) were suspended in RPMI 1640 medium (available from Bio-Whittaker Co., Ltd.) containing 10%(v/v) of fetal bovine serum, 2 mM of glutamine, 50 μM of 2-mercaptoethanol, 60 μg/ml of penicillin and 100 μg/ml of streptomycin.

The suspension of the THP-1 cell was subcultured at 37° C. under the atmosphere of 95% oxygen and 5% carbon dioxide. A portion of the subcultured suspension was centrifuged at 1200 rpm at room temperature for 3 minutes to recover the subcultured THP-1 cells.

The resulting THP-1 cells were resuspended in RPMI 1640 medium containing 2%(v/v) of fetal bovine serum, 2 mM of glutamine, 50 μM of 2-mercaptoethanol, 60 μg/ml of penicillin and 100 μg/ml of streptomycin so as to provide a final THP-1 cell concentration of $3 \times 10^6$ cells/ml.

The resuspension of the cell was dispensed in 0.5 ml portions to wells of a 24-well plate for cell culture. Then, each solution of the present Compounds 1–3 dissolved in DMSO at the respective specified concentrations was added in 2.5 μl portions to each well. The plate was incubated at 37° C. under the atmosphere of 95% oxygen and 5% carbon dioxide for one hour. Then, 12-o-tetradecanoylphorbol-13-acetate (PMA) and polyinosic acid were added to each well so as to provide final concentrations of 2 μg/ml and 200 μg/ml, respectively. The plate was incubated at 37° C. under the atmosphere of 95% oxygen and 5% carbon dioxide for 24 hours. After incubation, a supernatant was recovered from each well by means of Pipetteman available from Gilson Co., Ltd. Then, an amount of the IL-1β in the supernatant was assayed by means of the enzyme immunoassay kit available from Cayman Chemical Co., Ltd.

The results are summarized below, expressed in terms of $IC_{50}$ values in μM unit, wherein the amount of IL-1β produced at the time of no addition of the pyrrolidinone derivative is defined as 100 and the concentration of each test compound of the present invention to inhibit 50% the IL-1β production is defined as $IC_{50}$.

| Test compound | $IC_{50}$ (μM) |
| --- | --- |
| Compound 1 | 26 |
| Compound 2 | 86 |
| Compound 3 | 73 |
| Compound 4 | 73 |
| Compound 5 | 69 |
| Compound 9 | 13 |
| Compound 12 | 1.4 |
| Compound 13 | 48 |
| Compound 14 | 42 |

EXAMPLE 2

The pyrrolidinone derivatives of the present invention were evaluated for the activity to inhibit the release of TNFα, in accordance with the following method.

The THP-1 cells derived from human peripheral blood (ATCC TIB202) were suspended in RPMI 1640 medium (available from Bio-Whittaker Co., Ltd.) containing 10%(v/v) of fetal bovine serum, 2 mM of glutamine, 50 μM of 2-mercaptoethanol, 60 μg/ml of penicillin and 100 μg/ml of streptomycin.

The suspension of THP-1 cell was subcultured at 37° C. under the atmosphere of 95% oxygen and 5% carbon dioxide. A portion of the subcultured suspension was centrifuged at 1200 rpm at room temperature for 3 minutes to recover the subcultured THP-1 cells.

The resulting THP-1 cells were resuspended in RPMI 1640 medium containing 2%(v/v) of fetal bovine serum, 2 mM of glutamine, 50 µM of 2-mercaptoethanol, 60 µg/ml of penicillin and 100 µg/ml of streptomycin so as to provide a final THP-1 cell concentration of $3 \times 10^6$ cells/ml.

The resuspension of the cell was dispensed in 0.5 ml portions to wells of a 24-well plate for cell culture, and incubated at 37° C. for one hour. Each solution of the present pyrrolidinone derivatives dissolved in DMSO at the respective specified concentrations was added in 2.5 µl portions to each well. The plate was incubated at 37° C. under the atmosphere of 95% oxygen and 5% carbon dioxide for one hour. Then, PMA and polyinosic acid were added to each well so as to provide final concentrations of 2 µg/ml and 200 µg/ml, respectively. The plate was incubated at 37° C. under the atmosphere of 95% oxygen and 5% carbon dioxide for 24 hours. After incubation, a supernatant was recovered from each well by means of Pipetteman available from Gilson Co., Ltd. An amount of TNFα in the supernatant was assayed by means of the human TNFα ELISA kit available from Genzyme Co., Ltd.

The results are summarized below, expressed in terms of $IC_{50}$ values in µM unit, wherein the amount of TNFα released at the time of no addition of the pyrrolidinone derivatives is defined as 100 and the concentration of each test compound of the present invention to inhibit 50% the TNFα release is defined as $IC_{50}$.

| Test Compound | $IC_{50}$ (µM) |
| --- | --- |
| Compound 1 | 2.8 |
| Compound 5 | 16 |
| Compound 9 | 3.0 |
| Compound 12 | 4.6 |
| Compound 13 | 30 |

EXAMPLE 3

The present pyrrolidinone derivatives (Compounds 1–14) were evaluated for the cytotoxicity, in accordance with the following method.

The THP-1 cells derived from human peripheral blood (ATCC TIB202) were suspended in RPMI 1640 medium (available from Bio-Whittaker Co., Ltd.) containing 10%(v/v) of fetal bovine serum, 2 mM of glutamine, 50 µM of 2-mercaptoethanol, 60 µg/ml of penicillin and 100 µg/ml of streptomycin.

The suspension of THP-1 cell was subcultured at 37° C. under the atmosphere of 95% oxygen and 5% carbon dioxide. A portion of the subcultured suspension was centrifuged at 1200 rpm at room temperature for 3 minutes to recover the subcultured THP-1 cells. The resulting THP-1 cells were resuspended in RPMI 1640 medium containing 2%(v/v) of fetal bovine serum, 2 mM of glutamine, 50 µM of 2-mercaptoethanol, 60 µg/ml of penicillin and 100 µg/ml of streptomycin so as to provide a final THP-1 cell concentration of $1 \times 10^6$ cells/ml.

The resuspension of the cell was dispensed in 1 ml portions to wells of a 24-well plate for cell culture. Then, each solution of the present Compounds 1–14 dissolved in DMSO at the respective specified concentrations was added in 5 µl portions to each well. The plate was incubated at 37° C. under the atmosphere of 95% oxygen and 5% carbon dioxide for 24 hours. After incubation, 100 µl of Alamar Blue (available from Biosource Co., Ltd.) was added to each well and then incubation was further continued at 37° C. under the atmosphere of 95% oxygen and 5% carbon dioxide for 3 hours.

After incubation, a supernatant was recovered by means of the Pipetteman available from Gilson Co., Ltd. and determined for a difference in absorbances at 570 nm and 600 nm. The difference in absorbances at 570 nm and 600 nm for the test solution containing no pyrrolidinone derivative was used as a standard. If the difference in absorbance is significantly reduced upon the addition of the present pyrrolidinone derivatives, it is estimated that there is cytotoxicity.

The above test demonstrated that no cytotoxicity was found in Compounds 1–14 at the concentration up to 50 µM.

Preparation Example 1

Tablets were prepared using the following formulation per tablet.

| Tablets | |
| --- | --- |
| Compound 9 | 20 mg |
| Magnesium silicate | 20 mg |
| Lactose | 98.5 mg |
| Hydroxypropylcellulose | 7.5 mg |
| Magnesium stearate | 1 mg |
| Vegetable hardened oil | 3 mg |

Compound 9, magnesium silicate and lactose were blended and kneaded with an alcoholic solution containing hydroxypropylcellulose. The resulting mixture was granulated to a suitable particle size, dried and sized. Then, magnesium stearate and vegetable hardened oil were blended to form uniform granules and then the granules were formed to tablets by means of a rotary tableting machine, each tablet having a diameter of 7.0 mm, a weight of 150 mg and a hardness of 6 kg.

Preparation Example 2

| Granules | |
| --- | --- |
| Compound 9 | 10 mg |
| Magnesium oxide | 40 mg |
| Calcium hydrogenphosphate | 38 mg |
| Lactose | 10 mg |
| Hydroxypropylcellulose | 20 mg |

All the above components except for hydroxypropylcellulose were blended and then an alcoholic solution containing hydroxypropylcellulose was added and kneaded. The resulting mixture was granulated by means of an extrusion granulating machine and dried to form granules, which were then sized and passed through a 12 mesh sieve. The product left on a 48 mesh sieve was obtained as granules.

Preparation Example 3

| Syrups | |
| --- | --- |
| Compound 9 | 1.000 g |
| Sucrose | 30.000 g |
| 70 w/v % D-Sorbitol | 25.000 g |
| Ethyl p-hydroxybenzoate | 0.030 g |
| Propyl p-hydroxybenzoate | 0.015 g |
| Flavoring agent | 0.200 g |
| Glycerol | 0.150 g |

-continued

| Syrups | |
|---|---|
| 96% Ethanol | 0.500 g |
| Purified water | ad lib. |
| Total | 100 ml |

Sucrose, D-sorbitol, ethyl p-hydroxybenzoate, propyl p-hydroxybenzoate and Compound 9 were dissolved in 60 g of purified water (warm water). After cooling, a solution of the flavoring agent in glycerol and 96% ethanol was added. To the resulting mixture was added purified water to make it up to 100 ml.

Preparation Example 4

| Injections | |
|---|---|
| Hydrochloride of Compound 12 | 10.0 mg |
| Sodium chloride | 81.0 mg |
| Sodium bicarbonate | 8.40 mg |
| Distilled water for injection | ad lib. |
| Total | 10.0 ml |

Sodium bicarbonate, sodium chloride and hydrochloride of Compound 12 were dissolved in distilled water for injection to make up injections, each having a total volume of 10.0 ml.

Preparation Example 5

| Suppositories | |
|---|---|
| Compound 9 | 2 g |
| Macrogol 4000 (Polyethylene glycol) | 20 g |
| Glycerol | 78 g |
| Total | 100 g |

Compound 9 was dissolved in glycerol and then Macrogol 4000 was added. The mixture was dissolved under heat, poured into a suppository mold and then solidified by cooling to form suppositories, each weighing 1.5 g.

What is claimed is:

1. A method of preventing or treating a disease selected from the group consisting of chronic rheumatism and sepsis in a mammal in need thereof which comprises administering to the mammal an effective amount to prevent or treat said disease, of a compound of the formula

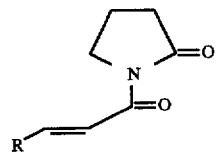

or the pharmacologically acceptable salts thereof wherein R represents a phenyl group; a phenyl group substituted by a $C_1$–$C_4$ alkoxy group or a nitro group; or a pyridyl group.

2. The method of claim 1 wherein R is phenyl.
3. The method of claim 1 wherein R is nitrophenyl.
4. The method of claim 1 wherein R is pyridyl.

* * * * *